United States Patent
Davis

(10) Patent No.: US 6,435,419 B1
(45) Date of Patent: Aug. 20, 2002

(54) LIQUID AIR FRESHENER DISPENSING DEVICE FOR A DUCT

(76) Inventor: Gordon D. Davis, 77 Stone Crescent SE., Medicine Hat Alberta (CA), T1B 3J5

(*) Notice: Subject to any disclaimer, the term of this patent is extended or adjusted under 35 U.S.C. 154(b) by 0 days.

(21) Appl. No.: 09/775,443

(22) Filed: Feb. 2, 2001

(51) Int. Cl.[7] .................................................. F24F 3/14
(52) U.S. Cl. ..................... 237/78 R; 239/34; 239/56; 261/DIG. 88; 454/337; 422/124
(58) Field of Search .......................... 237/78 R; 239/34, 239/56; 454/328, 110, 157, 291, 337; 261/DIG. 88; 422/123, 124

(56) References Cited

U.S. PATENT DOCUMENTS

| | | | | |
|---|---|---|---|---|
| 3,158,081 A | * | 11/1964 | Frost | 237/78 R |
| 3,203,594 A | * | 8/1965 | Jones | 454/157 |
| 4,159,672 A | * | 7/1979 | Garguilo et al. | 454/157 |
| 4,235,373 A | * | 11/1980 | Clark | 239/34 |
| 4,867,045 A | * | 9/1989 | Freedman | 454/157 |
| 4,903,583 A | * | 2/1990 | Frazier | 454/157 |
| 5,078,046 A | * | 1/1992 | Mascolo et al. | 454/157 |
| 5,882,256 A | * | 3/1999 | Shropshire | 454/157 |

* cited by examiner

Primary Examiner—Harold Joyce
Assistant Examiner—Derek S. Boles

(57) ABSTRACT

A liquid air freshener dispensing device for a duct for dispensing liquid freshener into air being heated and moved by a furnace. The liquid air freshener dispensing device for a duct includes a container having a top wall, a bottom wall and a peripheral wall extending between the top and bottom walls. A fragrant liquid is located in an interior of the container. An intake conduit extends through the top wall and into the interior of the housing such that a first end of the intake conduit is positioned in the housing and a second end of the intake conduit is located outside of the housing. A pump is in fluid communication with the second end of the intake conduit. The pump is operationally coupled to a power supply of a blower member. An exit conduit has a first end in fluid communication with the pump. The exit conduit extends into a duct such that a second end of the exit conduit is located in an interior space of the duct. The blower member blows air over a heating member and into the heating duct. The pump expels the fragrant fluid into the duct when the blower member is powered.

8 Claims, 3 Drawing Sheets

LIQUID AIR FRESHENER DISPENSING DEVICE FOR A DUCT

BACKGROUND OF THE INVENTION

1. Field of the Invention

The present invention relates to air freshener dispensers and more particularly pertains to a new liquid air freshener dispensing device for a duct for dispensing liquid freshener into air being heated and moved by a furnace.

2. Description of the Prior Art

The use of air freshener dispensers is known in the prior art. More specifically, air freshener dispensers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,018,266; U.S. Pat. No. 5,050,798; U.S. Pat. No. 4,574,491; U.S. Pat. No. 4,065,262; U.S. Pat. No. 3,861,052; and U.S. Des. Pat. No. 330,682.

While these devices fulfill their respective, particular objectives and requirements, the aforementioned patents do not disclose a new liquid air freshener dispensing device for a duct. The inventive device includes a container having a top wall, a bottom wall and a peripheral wall extending between the top and bottom walls. A fragrant liquid is located in an interior of the container. An intake conduit extends through the top wall and into the interior of the housing such that a first end of the intake conduit is positioned in the housing and a second end of the intake conduit is located outside of the housing. A pump is in fluid communication with the second end of the intake conduit. The pump is operationally coupled to a power supply of a blower member. An exit conduit has a first end in fluid communication with the pump. The exit conduit extends into a duct such that a second end of the exit conduit is located in an interior space of the duct. The blower member blows air over a heating member and into the heating duct. The pump expels the fragrant fluid into the duct when the blower member is powered.

In these respects, the liquid air freshener dispensing device for a duct according to the present invention substantially departs from the conventional concepts and designs of the prior art, and in so doing provides an apparatus primarily developed for the purpose of dispensing liquid freshener into air being heated and moved by a furnace.

SUMMARY OF THE INVENTION

In view of the foregoing disadvantages inherent in the known types of air freshener dispensers now present in the prior art, the present invention provides a new liquid air freshener dispensing device for a duct construction wherein the same can be utilized for dispensing liquid freshener into air being heated and moved by a furnace.

The general purpose of the present invention, which will be described subsequently in greater detail, is to provide a new liquid air freshener dispensing device for a duct apparatus and method which has many of the advantages of the air freshener dispensers mentioned heretofore and many novel features that result in a new liquid air freshener dispensing device for a duct which is not anticipated, rendered obvious, suggested, or even implied by any of the prior art air freshener dispensers, either alone or in any combination thereof.

To attain this, the present invention generally comprises a container having a top wall, a bottom wall and a peripheral wall extending between the top and bottom walls. A fragrant liquid is located in an interior of the container. An intake conduit extends through the top wall and into the interior of the housing such that a first end of the intake conduit is positioned in the housing and a second end of the intake conduit is located outside of the housing. A pump is in fluid communication with the second end of the intake conduit. The pump is operationally coupled to a power supply of a blower member. An exit conduit has a first end in fluid communication with the pump. The exit conduit extends into a duct such that a second end of the exit conduit is located in an interior space of the duct. The blower member blows air over a heating member and into the heating duct. The pump expels the fragrant fluid into the duct when the blower member is powered.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new liquid air freshener dispensing device for a duct apparatus and method which has many of the advantages of the air freshener dispensers mentioned heretofore and many novel features that result in a new liquid air freshener dispensing device for a duct which is not anticipated, rendered obvious, suggested, or even implied by any of the prior art air freshener dispensers, either along or in any combination thereof.

It is another object of the present invention to provide a new liquid air freshener dispensing device for a duct which may be easily and efficiently manufactured and marketed.

It is a further object of the present invention to provide a new liquid air freshener dispensing device for a duct which is of a durable and reliable construction.

An even further object of the present invention is to provide a new liquid air freshener dispensing device for a duct which is susceptible of a low cost of manufacture with regard to both materials and labor, and which accordingly is then susceptible of low prices of sale to the consuming public, thereby making such liquid air freshener dispensing device for a duct economically available to the buying public.

Still yet another object of the present invention is to provide a new liquid air freshener dispensing device for a duct which provides in the apparatuses and methods of the prior art some of the advantages thereof, while simultaneously overcoming some of the disadvantages normally associated therewith.

Still another object of the present invention is to provide a new liquid air freshener dispensing device for a duct for dispensing liquid freshener into air being heated and moved by a furnace.

Yet another object of the present invention is to provide a new liquid air freshener dispensing device for a duct which includes a container having a top wall, a bottom wall and a peripheral wall extending between the top and bottom walls. A fragrant liquid is located in an interior of the container. An intake conduit extends through the top wall and into the interior of the housing such that a first end of the intake conduit is positioned in the housing and a second end of the intake conduit is located outside of the housing. A pump is in fluid communication with the second end of the intake conduit. The pump is operationally coupled to a power supply of a blower member. An exit conduit has a first end in fluid communication with the pump. The exit conduit extends into a duct such that a second end of the exit conduit is located in an interior space of the duct. The blower member blows air over a heating member and into the heating duct. The pump expels the fragrant fluid into the duct when the blower member is powered.

Still yet another object of the present invention is to provide a new liquid air freshener dispensing device for a duct that may be retrofitted to existing duct and furnace devices.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
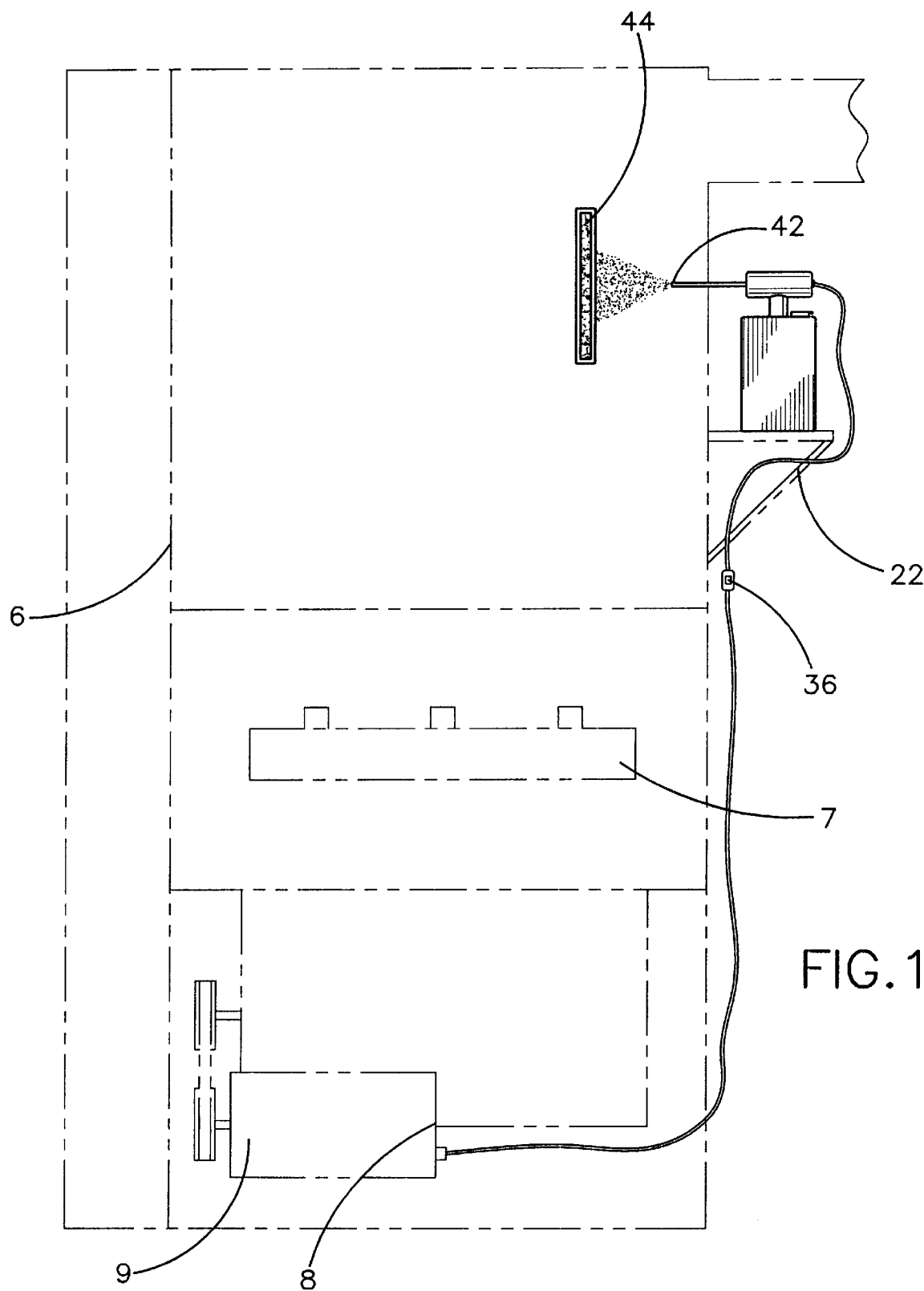
FIG. 1 is a schematic side view of a new liquid air freshener dispensing device for a duct according to the present invention.
Figure 2:
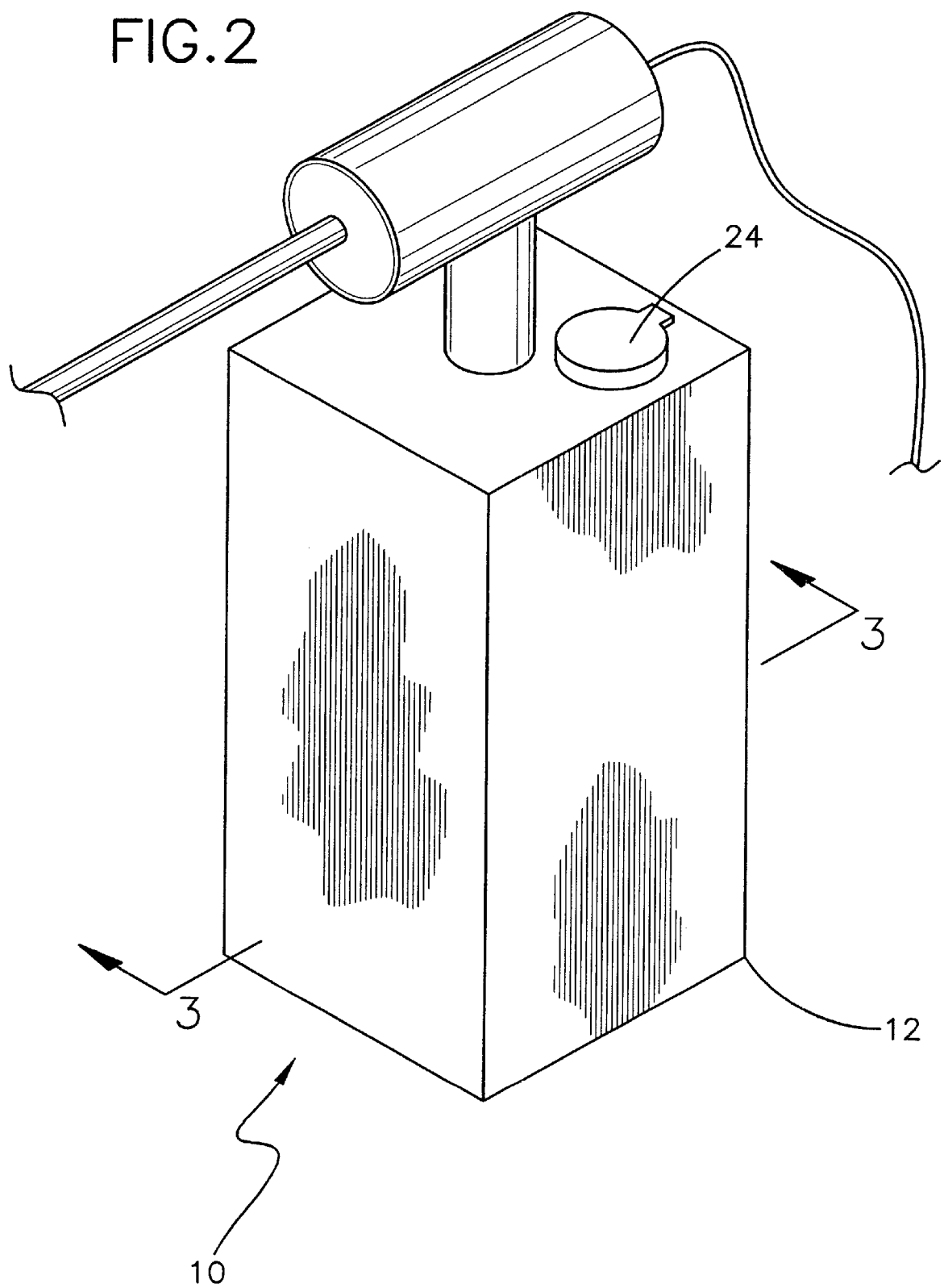
FIG. 2 is a schematic perspective view of the present invention.
Figure 3:
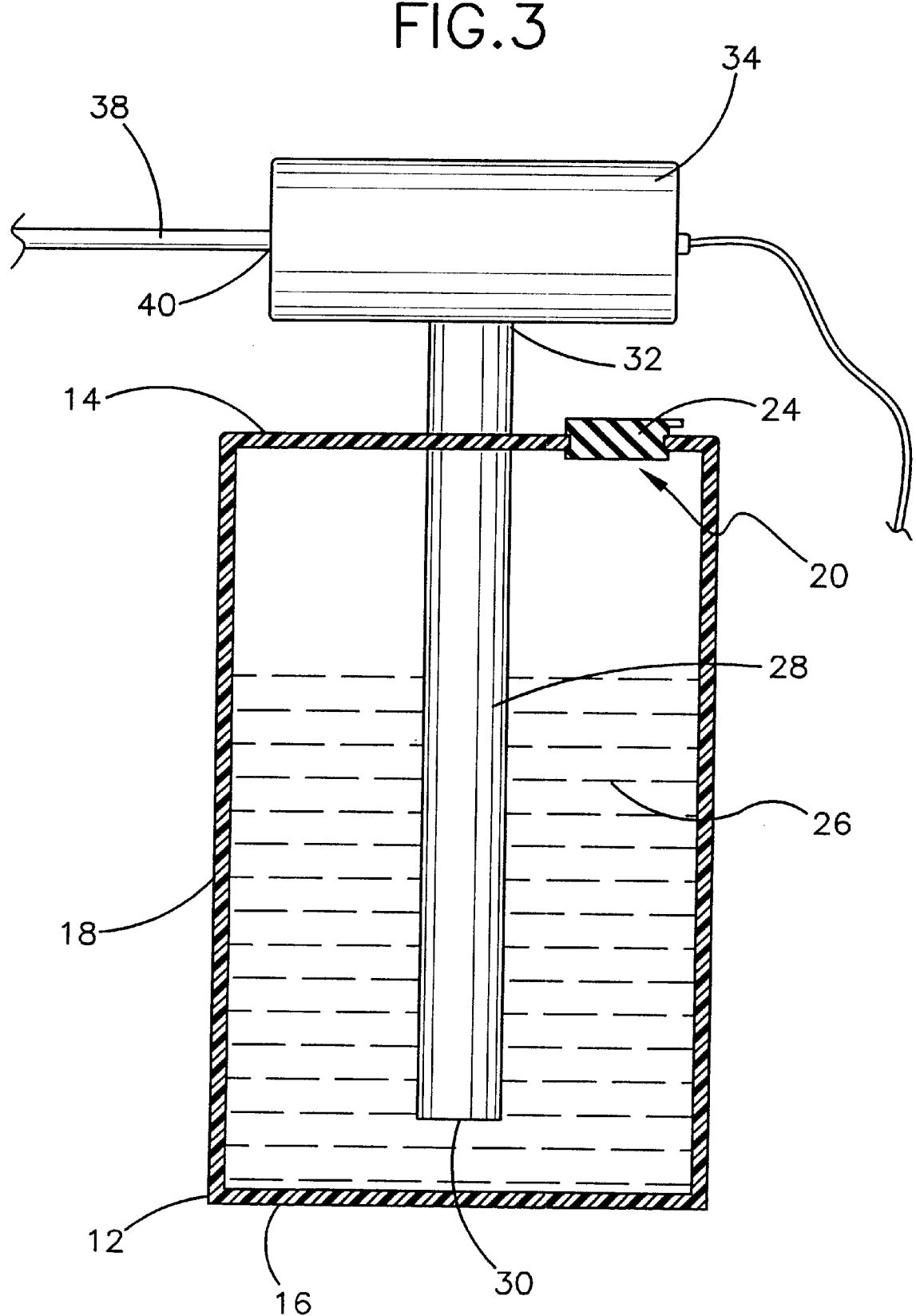
FIG. 3 is a schematic cross-sectional view taken along line 3—3 in FIG. 2 of the present invention.

With reference now to the drawings, and in particular to FIGS. 1 through 3 thereof, a new liquid air freshener dispensing device for a duct embodying the principles and concepts of the present invention and generally designated by the reference numeral 10 will be described.

As best illustrated in FIGS. 1 through 3, the liquid air freshener dispensing device 10 for a duct generally comprises a device that is removably attachable to a duct 6. The duct 6 is in communication with a heating member 7 and a blowing member 8. The blowing member 8 blows air across the heating member 7 and into the duct 6, and generally defines a conventional heating furnace.

The device 10 includes a container 12 having a top wall 14, a bottom wall 16 and a peripheral wall 18 extending between the top 14 and bottom 16 walls. The top wall 14 has an opening 20 therein. Ideally, a platform 22 is coupled to the duct 6 for positioning the container 12 thereon. A cover portion 24 is removably positioned in the opening 20 for selectively closing the opening 20.

A fragrant liquid 26 is located in an interior of the container 12. The container 12 may be filled by pouring the liquid 26 through the opening 20. The liquid 26 may be any conventional type of liquid air freshener.

An intake conduit 28 extends through the top wall 14 and into the interior of the housing 12 such that a first end 30 of the intake conduit 28 is positioned in the housing and a second end 32 of the intake conduit 28 is located outside of the housing 12. A pump 34 is in fluid communication with the second end 32 of the intake conduit 28. The pump 34 preferably comprises an electric pump. The pump 34 is operationally coupled to a power supply 9 of the blower member 8. A switch 36 selectively turns the pump 34 on and off is operationally coupled to the pump 34. An exit conduit 38 has a first end 40 in fluid communication with the pump 34. The exit conduit 38 extends into the duct 6 such that a second end 42 of the exit conduit 38 is located in an interior space of the duct 6. Ideally, a filter 44 is removably positioned in the duct 6 such that the second end 42 of the exit conduit 38 is directed toward the filter 44. The filter 44 preferably comprises a steel wire mesh, and may be slidably mounted in the perimeter wall of the duct.

In use, the pump 34 extracts the fragrant fluid 26 from the container 12 and expels the fragrant fluid 26 into the duct 6 when a power supply 9 powers the blower member 8. In this manner, the pump 34 only operates when the blower 8, such as a fan, is blowing air past the exit conduit 38. The switch 36 overrides the power supply from the blower member 8 if the user does not want to operate the pump 34. The filter 44 catches the liquid 26 so that it does not coat the inner surfaces of the duct 6 and the filter 44 is removable for cleaning.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specifications are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A duct air freshening device, said device being removably attachable to a duct, said duct being in communication with a heating member and a blowing member, wherein the blowing member blows air across the heating member and into said duct, said device comprising:

a container having a top wall, a bottom wall and a peripheral wall extending between said top and bottom walls;

a fragrant liquid being located in an interior of said container;

an intake conduit extending through said top wall and into said interior of said housing such that a first end of said intake conduit is positioned in said housing and a second end of said intake conduit is located outside of said housing;

a pump being in fluid communication with said second end of said intake conduit, said pump being operationally coupled to a power supply of said blower member; and an exit conduit having a first end in fluid communication with said pump, said exit conduit extending into said duct such that a second end of said exit conduit is located in an interior space of said duct, said second end of said exit conduit atomizing fragrant liquid passing therethrough;

a filter being removably positioned in said duct such that said second end of said exit conduit is directed toward said filter, said filter being positioned such that said second of said exit conduit is oriented substantially perpendicular to a face of said filter, said second end of said exit conduit being spaced from said face of said filter such that atomized fragrant liquid strikes said face of said filter.

2. The duct air freshening device as in claim 1, wherein said top wall has an opening therein, a cover portion being removably positioned in said opening for selectively closing said opening.

3. The duct air freshening device as in claim 1, further including a switch for selectively turning said pump on and off being operationally coupled to said pump.

4. A duct air freshening device, said device being removably attachable to a duct, said duct being in communication with a heating member and a blowing member, wherein the blowing member blows air across the heating member and into said duct, said device comprising:

a container having a top wall, a bottom wall and a peripheral wall extending between said top and bottom walls, said top wall having an opening therein;

a cover portion being removably positioned in said opening for selectively closing said opening;

a fragrant liquid being located in an interior of said container;

an intake conduit extending through said top wall and into said interior of said housing such that a first end of said intake conduit is positioned in said housing and a second end of said intake conduit is located outside of said housing;

a pump being in fluid communication with said second end of said intake conduit, said pump comprising an electric pump, said pump being operationally coupled to a power supply of said blower member;

a switch for selectively turning said pump on and off being operationally coupled to said pump;

an exit conduit having a first end in fluid communication with said pump, said exit conduit extending into said duct such that a second end of said exit conduit is located in an interior space of said duct, said second end of said exit conduit atomizing fragrant liquid passing therethrough;

a filter being removably positioned in said duct such that said second end of said exit conduit is directed toward said filter, said filter comprising a wire mesh, said wire mesh comprising a steel material, said second end of said exit conduit being spaced from a face of said filter such that atomized fragrant liquid strikes said face of said filter; and wherein said pump extracts said fragrant fluid from said container and expels said fragrant fluid into said duct when a power supply powers said blower member.

5. A duct air freshening device, said device being removably attachable to a duct, said duct being in communication with a blowing member, wherein the blowing member blows air into said duct, said device comprising;

a container having a top wall, a bottom wall and a peripheral wall extending between said top and bottom walls;

a fragrant liquid being located in an interior of said container;

a pump being in fluid communication with said container, said pump operationally coupled to a power supply of the blower member; and an exit conduit having a first end in fluid communication with said pump, said exit conduit extending into said duct such that a second end of said exit conduit is located in an interior space of said duct, said second end of said exit conduit atomizing fragrant liquid passing therethrough; and a filter being removably positioned in said duct such that said second end of said exit conduit is directed toward said filter, said second end of said exit conduit being spaced from a face of said filter such that atomized fragrant liquid strikes said face of said filter.

6. The duct air freshening device as in claim 5, wherein said filter is positioned such that said second of said exit conduit is oriented substantially perpendicular to a face of said filter.

7. The duct air freshening device as in claim 5 wherein said top wall has an opening therein, a cover portion being removably positioned in said opening for selectively closing said opening.

8. The duct air freshening device as in claim 5, further including a switch for selectively turning said pump on and off being operationally coupled to said pump.

* * * * *